(12) United States Patent
Wang et al.

(10) Patent No.: US 11,497,729 B2
(45) Date of Patent: Nov. 15, 2022

(54) METHODS AND MATERIALS FOR TREATING CANCER

(71) Applicant: Mayo Foundation for Medical Education and Research, Rochester, MN (US)

(72) Inventors: Liewei Wang, Rochester, MN (US); Matthew P. Goetz, Rochester, MN (US); Judy C. Boughey, Rochester, MN (US); Jia Yu, Rochester, MN (US); Bo Qin, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 839 days.

(21) Appl. No.: 16/316,182

(22) PCT Filed: Jul. 7, 2017

(86) PCT No.: PCT/US2017/041120
§ 371 (c)(1),
(2) Date: Jan. 8, 2019

(87) PCT Pub. No.: WO2018/009812
PCT Pub. Date: Jan. 11, 2018

(65) Prior Publication Data
US 2021/0283101 A1 Sep. 16, 2021

Related U.S. Application Data

(60) Provisional application No. 62/360,169, filed on Jul. 8, 2016.

(51) Int. Cl.
*A61K 31/381* (2006.01)
*A61P 35/00* (2006.01)
*C07K 16/32* (2006.01)

(52) U.S. Cl.
CPC .......... *A61K 31/381* (2013.01); *A61P 35/00* (2018.01); *C07K 16/32* (2013.01)

(58) Field of Classification Search
CPC ....... A61K 45/06; A61K 31/381; C07K 16/32
See application file for complete search history.

(56) References Cited

U.S. PATENT DOCUMENTS

| | | |
|---|---|---|
| 2011/0177105 A1 | 7/2011 | Lopez et al. |
| 2012/0114765 A1 | 5/2012 | Cao et al. |
| 2014/0179618 A1 | 6/2014 | Nuber |
| 2014/0371247 A1 | 12/2014 | Colland et al. |
| 2015/0072973 A1 | 3/2015 | Lopez et al. |
| 2016/0185785 A1 | 6/2016 | Ioannidis et al. |
| 2016/0185786 A1 | 6/2016 | Ioannidis et al. |

FOREIGN PATENT DOCUMENTS

| | | |
|---|---|---|
| WO | WO 2016/102517 | 6/2016 |
| WO | WO 2016/150800 | 9/2016 |

OTHER PUBLICATIONS

Parakh. Cancer Treatment Reviews, 2017, 59, 1-21 (Year: 2017).*
Baselga et al., "Pertuzumab plus Trastuzumab plus Docetaxel for Metastatic Breast Cancer," N. Engl. J. Med., 366(2):109-19, Jan. 2012.
Bullock, "FOXO Factors and Breast Cancer: Outfoxing Endocrine Resistance," Endocrine-Related Cancer,23(2):R113-30, Nov. 2015.
Citri and Yarden, "EGF-ERBB signalling: towards the systems level.," Nat. Rev. Mol. Cell Biol., 7(7):505-16, Jul. 2006.
Colland, "The therapeutic potential of deubiquitinating enzyme inhibitors," Biochem. Soc. Trans., 38(Pt.1): 137-43, Feb. 2010.
Extended European Seach Report in EP Appln. No. EP17824987, dated Apr. 23, 2019.
Fan et al. "USP7 Inhibitor P22077 Inhibits Neuroblastoma Growth via Inducing p53-Mediated Apoptosis," Cell Death Dis., 4(10):e867, Oct. 2013.
Geyer et al., "Lapatinib plus capecitabine for HER2-positive advanced breast cancer," N. Engl. J. Med., 355(26):2733-43, Dec. 2006.
Gullick, "Update on HER-2 as a target for cancer therapy: alternative strategies for targeting the epidermal growth factor system in cancer," Breast Cancer Res., 3(6):390-4, Dec. 2001.
Huang and D'Andrea, "HAUSP hunting the FOX(O)," Nat. Cell Biol., 8(10):1043-5, Oct. 2006.
Li et al., "A dynamic role of HAUSP in the p53-Mdm2 pathway," Mol. Cell, 13(6):879-86, Mar. 2004.
Li et al., "Deubiquitination of p53 by HAUSP is an important pathway for p53 stabilization," Nature, 416(6881):648-53, Mar. 2002.
Linardou et al., "Somatic EGFR mutations and efficacy of tyrosine kinase inhibitors in NSCLC," Nature Rev. Clin. Oncol., 6(6):352-66, Jun. 2009.
Meulmeester et al., "Loss of HAUSP-mediated deubiquitination contributes to DNA damage-induced destabilization of Hdmx and Hdm2," Mol. Cell, 18(5):565-76, May 2005.
Nahta and Esteva,"Herceptin: mechanisms of action and resistance," Cancer Lett., 232(2):123-38, Feb. 2006.
Nahta et al., "Mechanisms of Disease: understanding resistance to HER2-targeted therapy in human breast cancer," Nat. Clin. Pract. Oncol., 3(5):269-80, May 2006.

(Continued)

*Primary Examiner* — Noble E Jarrell
(74) *Attorney, Agent, or Firm* — Fish & Richardson P.C.

(57) ABSTRACT

This document provides methods and materials involved in treating cancer. For example, methods and materials for using an inhibitor of USP7 polypeptide to increase the sensitivity of cancer cells (e.g., CD340$^+$ cancer cells such as HER2$^+$ cancer cells) to treatment with an inhibitor of a CD340 polypeptide (e.g., an inhibitor of a HER2 polypeptide) are provided. Methods and materials for using USP7 polypeptide inhibitors in combination with CD340 polypeptide inhibitors to treat cancer (e.g., HER2$^+$ breast cancer that was refractory to trastuzumab alone treatment) are provided.

7 Claims, 6 Drawing Sheets

(56) References Cited

OTHER PUBLICATIONS

PCT International Preliminary Report on Patentability in International Appln. No. PCT/US2017/041120, 6 pages, dated Jan. 8, 2019.
PCT International Search Report and Written Opinion in International Appln. No. PCT/US2017/041120, 8 pages, dated Sep. 21, 2017.
Sacco et al., "Emerging Roles of Deubiquitinases in Cancer-Associated Pathways," iUBMB Life, 62(2):140-57, Jan. 2010.
Slamon et al., "Use of Chemotherapy plus a Monoclonal Antibody against HER2 for Metastatic Breast Cancer That Overexpresses ELER2," N. Engl. J. Med., 344(11):783-92, Mar. 2001.
Soule et al., "HER-2/neu expression in germ cell tumours ," J. Clin. Pathol., 55(9):656-8, Sep. 2002.
Sun and Dai, "Deubiquitinating enzyme regulation of the p53 pathway: A lesson from Otubl," World J. Biol. Chem., 5(2):75-84, May 2014.
Swain et al., "Pertuzumab, trastuzumab, and docetaxel for HER2-positive metastatic breast cancer (CLEOPATRA study): overall survival results from a randomised, double-blind, placebo-controlled, phase 3 study," Lancet Oncol., 14(6):461-71, May 2013.
Van der Horst et al., "FOXO4 transcriptional activity is regulated by monoubiquitination and USP7/HAUSP," Nat. Cell Biol., 8(10):1064-73, Sep. 2006.
Verma et al., "Trastuzumab Emtansine for HER2-Positive Advanced Breast Cancer," N. Engl. J. Med., 367(19):1783-91, Nov. 2012.
Yang et al., "Constitutively active FOXO4 inhibits Akt activity, regulates p27 Kip1 stability, and suppresses HER-mediated tumorigenicity," Oncogene, 24:1924-35, Jan. 2005.
Zhou et al., "HER-2/neu induces p53 ubiquitination via Akt-mediated MDM2 phosphorylation," Nat. Cell Biol., 3:973-82, Nov. 2001.

* cited by examiner

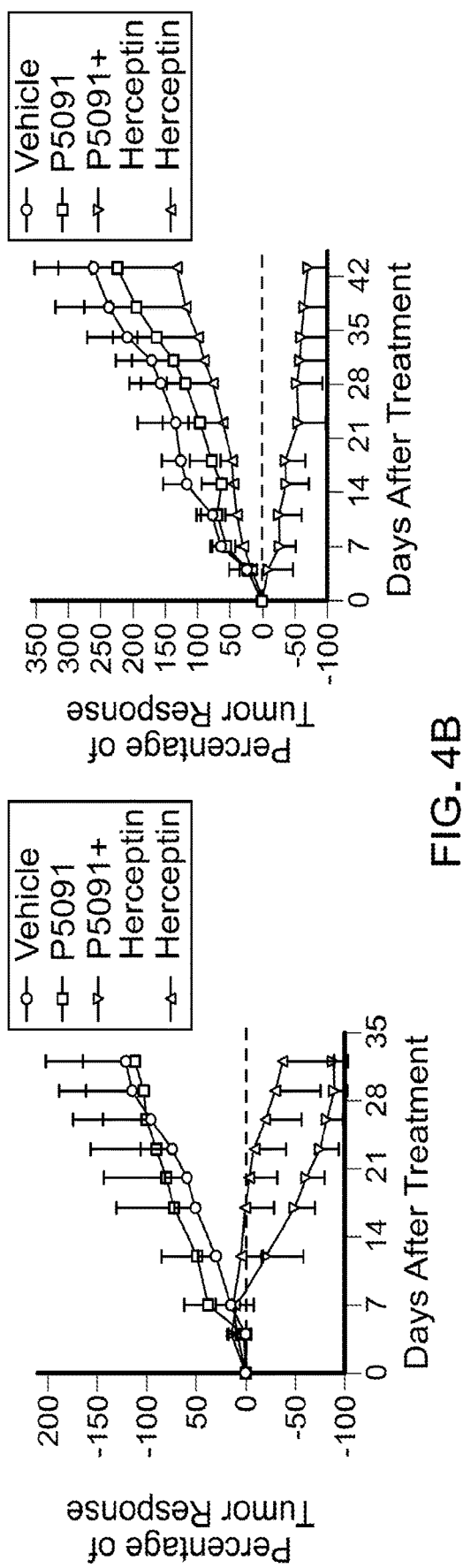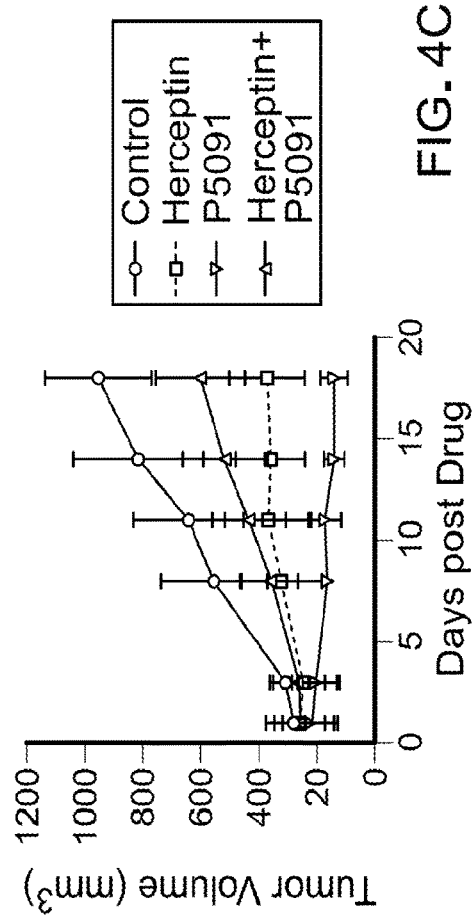
FIG. 4B
FIG. 4C

METHODS AND MATERIALS FOR TREATING CANCER

CROSS-REFERENCE TO RELATED APPLICATIONS

This application is a National Stage application under 35 U.S.C. § 371 of International Application No. PCT/US2017/041120, having an International Filing Date of Jul. 7, 2017, which claims priority to U.S. Application Ser. No. 62/360,169, filed on Jul. 8, 2016. The disclosures of the prior applications are considered part of the disclosure of this application, and are incorporated in their entirety into this application.

BACKGROUND

1. Technical Field

This document relates to methods and materials involved in treating cancer. For example, this document provides methods and materials for using an inhibitor of an ubiquitin-specific protease 7 (USP7) polypeptide to increase the sensitivity of cancer cells (e.g., CD340+ cancer cells such as human epidermal growth factor receptor 2 (HER2)-positive cancer cells) to treatment with an inhibitor of a CD340 polypeptide (e.g., an inhibitor of a HER2 polypeptide).

2. Background Information

Cancer is the second-leading cause of death in the United States. One example of cancer is breast cancer, which develops from breast tissue and is the most common invasive cancer in women. Breast cancer is usually treated with surgery, which may be followed by chemotherapy or radiation therapy, or both chemotherapy and radiation therapy.

About 20% of breast cancer tumors overexpress HER2 (as known as ErbB2 or CD340), which is associated with a more aggressive clinical phenotype and with a poorer prognosis (Soule et al., *J. Clin. Pathol.*, 55(9):656-8 (2002)). The development of trastuzumab, an immunoglobulin G monoclonal antibody directed against HER2, changed the treatment paradigm for this disease (Slamon et al., *N. Engl. J. Med.*, 344(11):783-92 (2001)). Since then, great advances in HER2-targeting therapies have been made, with three additional agents approved by the FDA: pertuzumab, lapatinib, and trastuzumab emtansine (T-DM1), converting HER2-positive breast cancer into a highly treatable disease, with extended survival for some patients.

About 15-20% of patients still do not respond to anti-HER2 therapy (Nahta and Esteva, *Cancer Lett.*, 232(2):123-38 (2006)). Furthermore, despite advances in the management of metastatic HER2-positive breast cancer, response rates in the first-line setting range from 50% to 80%, and only from 20% to 40% in the second-line setting, with most patients eventually succumbing to their disease (Slamon et al., *N. Engl. J. Med.*, 344(11):783-92 (2001); Geyer et al., *N. Engl. J. Med.*, 355(26):2733-43 (2006); Baselga et al., *N. Engl. J. Med.*, 366(2):109-19 (2012); Swain et al., *Lancet Oncol.*, 14(6):461-71 (2013); and Verma et al., *N. Engl. J. Med.*, 367(19):1783-91 (2012)).

SUMMARY

This document provides methods and materials for treating cancer. For example, this document provides methods and materials for using an inhibitor of an USP7 polypeptide to increase the sensitivity of cancer cells (e.g., CD340+ or HER2+ cancer cells) to treatment with an inhibitor of a CD340 polypeptide (e.g., an inhibitor of an HER2 polypeptide). As described herein, an inhibitor of an USP7 polypeptide can be administered to a mammal (e.g., a human) to increase the sensitivity of the mammal's CD340+ or HER2+ cancer cells to an inhibitor of a CD340 or HER2 polypeptide. After the sensitivity of the mammal's CD340+ or HER2+ cancer cells to a CD340 or HER2 polypeptide inhibitor is increased, a CD340 or HER2 polypeptide inhibitor (e.g., Herceptin) can be administered to the mammal to reduce the number of cancer cells within the mammal. In some cases, an USP7 polypeptide inhibitor can be administered together as a combination with a CD340 polypeptide inhibitor (e.g., an HER2 polypeptide inhibitor such as Herceptin) to reduce the number of cancer cells within the mammal. In some cases, an USP7 polypeptide inhibitor can be administered within the same week (or within the same day) with a CD340 polypeptide inhibitor (e.g., an HER2 polypeptide inhibitor such as Herceptin) to reduce the number of cancer cells within the mammal.

In some cases, the number of cancer cells within a mammal treated with both an USP7 polypeptide inhibitor and a CD340 polypeptide inhibitor can be reduced to a level that is more than the level of reduction observed in comparable mammals treated with the USP7 polypeptide inhibitor alone or treated with the CD340 polypeptide inhibitor alone.

In general, one aspect of this document features a method for treating cancer in a mammal. The method comprises, or consists essentially of, (a) administering an USP7 polypeptide inhibitor to the mammal, and (b) administering a CD340 polypeptide inhibitor to the mammal, wherein the number of cancer cells within the mammal is reduced to a greater level than the level observed in a comparable mammal administered the CD340 polypeptide inhibitor in the absence of administration of the USP7 polypeptide inhibitor. The mammal can be a human. The cancer can be breast cancer. The cancer can be a HER2+ cancer. The cancer can be resistant to trastuzumab when administered as the sole active ingredient. The USP7 polypeptide inhibitor can be P005091. The CD340 polypeptide inhibitor can be trastuzumab.

In another aspect, this document features a method for treating cancer in a mammal. The method comprises, or consists essentially of, (a) administering an USP7 polypeptide inhibitor to the mammal under conditions wherein the sensitivity of cancer cells within the mammal to a CD340 polypeptide inhibitor treatment is increased, and (b) administering, after at least about two hours (e.g., after at least about three hours, after at least about five hours, after at least about 12 hours, after at least about 24 hours, after at least about 36 hours, or after at least 48 three hours) of administering the USP7 polypeptide inhibitor to the mammal, a CD340 polypeptide inhibitor to the mammal under conditions wherein the number of cancer cells within the mammal is reduced. The mammal can be a human. The cancer can be breast cancer. The cancer can be a HER2+ cancer. The cancer can be resistant to trastuzumab when administered as the sole active ingredient. The USP7 polypeptide inhibitor can be P005091. The CD340 polypeptide inhibitor can be trastuzumab.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 4A-C. P005091 increases the efficacy of the HER2 inhibitor, trastuzumab, in HER2$^+$ breast cancer cells, xenografts, and patient derived xenograft (PDX) models. (A) P005091 sensitizes four different HER2$^+$ breast cancer cells to trastuzumab treatment. (B) Parent BT474 HER2$^+$ breast cancer cells and BT474 HER2 resistant cells were used to generate xenograft mice models. Treatment of both xenograft models showed that the combination of P005091 and trastuzumab significantly inhibited tumor growth compared with either treatment alone. (C) One HER2$^+$ PDX model shows a more sensitive phenotype to the combination treatment.

DETAILED DESCRIPTION

Figure 1:
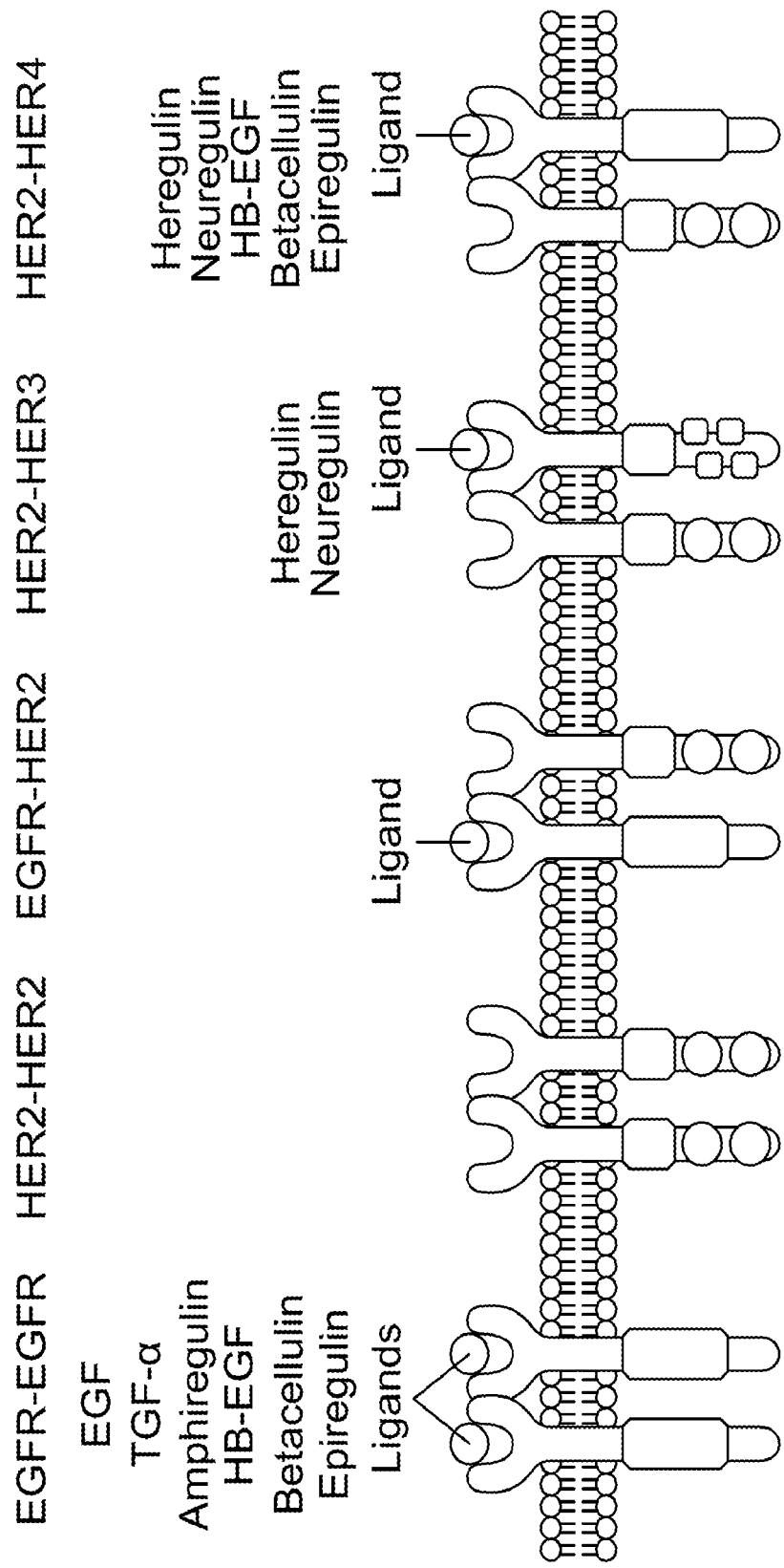
FIG. 1 is a schematic of HER family members and their known ligands (Linardou, *Nature Rev. Clin. Oncol.*, 6(6): 352-66 (2009)).

This document provides methods and materials for treating cancer. For example, this document provides methods and materials for using an inhibitor of an USP7 polypeptide to increase the sensitivity of cancer cells to treatment with an inhibitor of a CD340 polypeptide. Once the sensitivity of the mammal's cancer cells to a CD340 polypeptide inhibitor is increased, a CD340 polypeptide inhibitor can be administered to the mammal to reduce the number of cancer cells within the mammal. In some cases, a mammal having cancer can be treated with both an USP7 polypeptide inhibitor and a CD340 polypeptide inhibitor under conditions wherein the number of cancer cells within a mammal is reduced to a level that is more than the level of reduction observed in comparable mammals treated with the USP7 polypeptide inhibitor alone or treated with the CD340 polypeptide inhibitor alone.

Any type of mammal having cancer can be treated as described herein. For example, humans and other primates such as monkeys having cancer can be treated with one or more inhibitors of an USP7 polypeptide to increase the sensitivity of cancer cells to treatment with an inhibitor of a USP7 polypeptide together with and/or followed by treatment with one or more CD340 polypeptide inhibitors to reduce the number of cancer cells present within the mammal. In some cases, dogs, cats, horses, cows, pigs, sheep, mice, and rats can be treated with one or more USP7 polypeptide inhibitors together with and/or followed by one or more CD340 polypeptide inhibitors as described herein.

Any appropriate cancer can be treated as described herein. For example, breast cancer, ovarian cancer, gastrointestinal cancer, stomach cancer, or salivary duct carcinomas can be treated with one or more USP7 polypeptide inhibitors together with and/or followed by one or more CD340 polypeptide inhibitors as described herein. In some cases, a mammal (e.g., a human) having a HER positive cancer such as a HER1$^+$, HER2$^+$, HER3$^+$, and/or HER4$^+$ cancer (e.g., a HER2$^+$ breast cancer) can be administered one or more USP7 polypeptide inhibitors in combination with one or more CD340 polypeptide inhibitors. In some cases, the one or more USP7 polypeptide inhibitors and one or more CD340 polypeptide inhibitors can be administered sequentially, with the USP7 polypeptide inhibitor(s) being administered first or with the CD340 polypeptide inhibitor(s) being administered first. In some cases, a cancer resistant to treatment with a CD340 polypeptide inhibitor (e.g., Herceptin) such as Herceptin-resistant breast cancer can be treated using both an USP7 polypeptide inhibitor and a CD340 polypeptide inhibitor either in combination or sequentially.

Any appropriate method can be used to identify a mammal having cancer. For example, imaging techniques and biopsy techniques can be used to identify mammals (e.g., humans) having cancer (e.g., breast cancer). Any appropriate method can be used to identify the CD340 or HER (e.g., HER2) status of a mammal's cancer. For example, immunological techniques such as staining techniques using anti-CD340 antibodies can be used to identify mammals (e.g., humans) having HER2$^+$ cancer (e.g., HER2$^+$ breast cancer).

Once identified as having cancer (e.g., a CD340$^+$ cancer such as HER2$^+$ breast cancer), the mammal can be administered or instructed to self-administer (a) an USP7 polypeptide inhibitor to increase the sensitivity of cancer cells to treatment with an inhibitor of a CD340 polypeptide, (b) both an USP7 polypeptide inhibitor and a CD340 polypeptide inhibitor in combination, or (c) both an USP7 polypeptide inhibitor and a CD340 polypeptide inhibitor sequentially. When administered sequentially, the USP7 polypeptide inhibitor can be administered first. In some cases, when administered sequentially, the CD340 polypeptide inhibitor can be administered first.

Figures 3A, 3B:
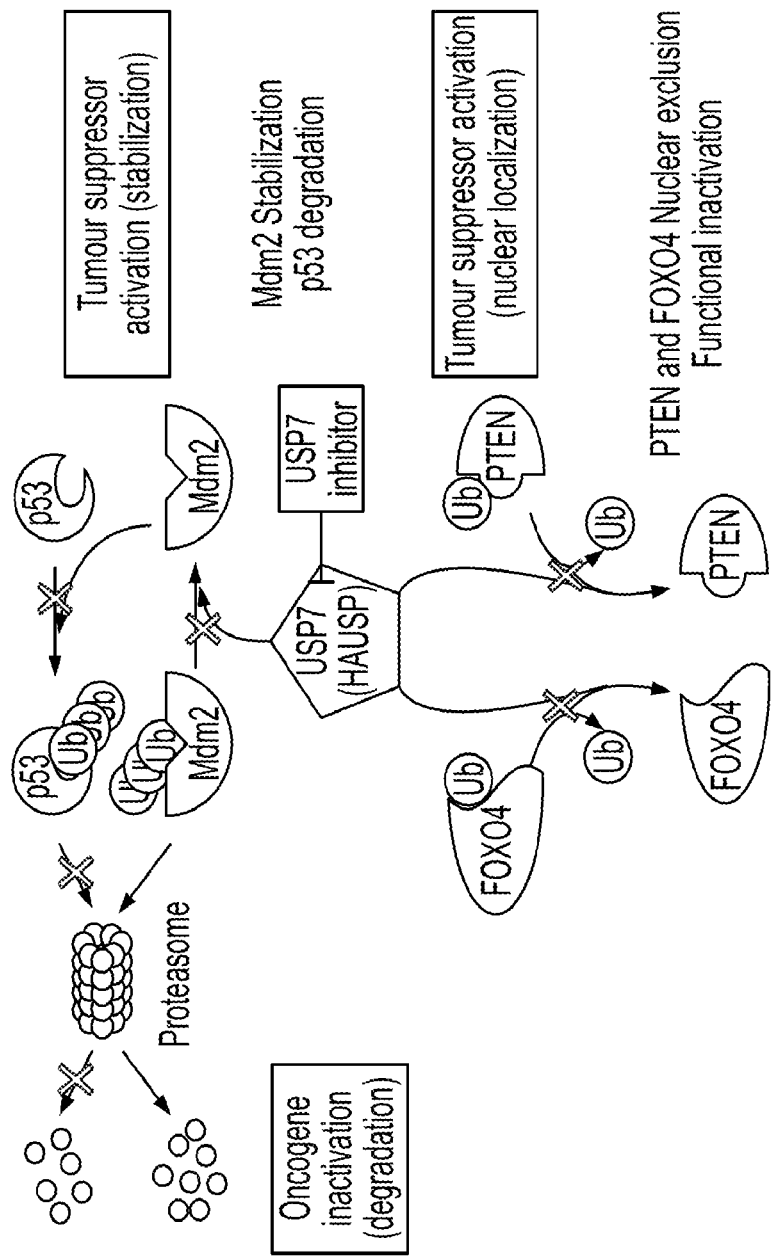
FIG. 3A is a diagram of the domain structure of USP7/HAUSP and USP7 interacting partners/substrates.
FIG. 3B is a schematic showing the involvement of USP7 in the regulation of function and stabilization of tumor suppressors and oncogenes (Colland, *Biochem. Soc. Trans.*, 38(Pt 1):137-43 (2010)).

Examples of USP7 polypeptide inhibitors include, without limitation, 1-[5-(2,3-dichlorophenyl)sulfanyl-4-nitrothiophen-2-yl]ethanone (also known as P005091 or P5091), HBX 41,108, and p22077 (USP7/USP47 inhibitor). In some cases, a USP7 inhibitor described elsewhere (see, e.g., van der Horst et al., *Nat. Cell Biol.*, 8(10):1064-73 (2006), Huang and D'Andrea, *Nat. Cell Biol.*, 8(10):1043-5 (2006), U.S. Patent Application Publication No. 2011/0177105, U.S. Patent Application Publication No. 2016/0185785, and U.S. Patent Application Publication No. 2016/0185786). A schematic showing the activity domain structure and interacting partners of USP7 polypeptides is set forth in FIG. 3.

In some cases, two or more USP7 polypeptide inhibitors (e.g., two, three, four, five, or more USP7 polypeptide inhibitors) can be administered to a mammal to increase the sensitivity of cancer cells to treatment with an inhibitor of a CD340 polypeptide. In some cases, two or more USP7 polypeptide inhibitors (e.g., two, three, four, five, or more USP7 polypeptide inhibitors) can be administered with one or more CD340 polypeptide inhibitors to a mammal (in combination or sequentially) to treat cancer more effectively than if either the USP7 polypeptide inhibitors were administered in the absence of CD340 polypeptide inhibitors or the CD340 polypeptide inhibitors were administered in the absence of USP7 polypeptide inhibitors.

In some cases, one or more USP7 polypeptide inhibitors can be formulated into a pharmaceutically acceptable composition for administration to a mammal having cancer (e.g., CD340$^+$ cancer such as HER2$^+$ breast cancer). For example, a therapeutically effective amount of an USP7 polypeptide inhibitor (e.g., P005091) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Figure 2:
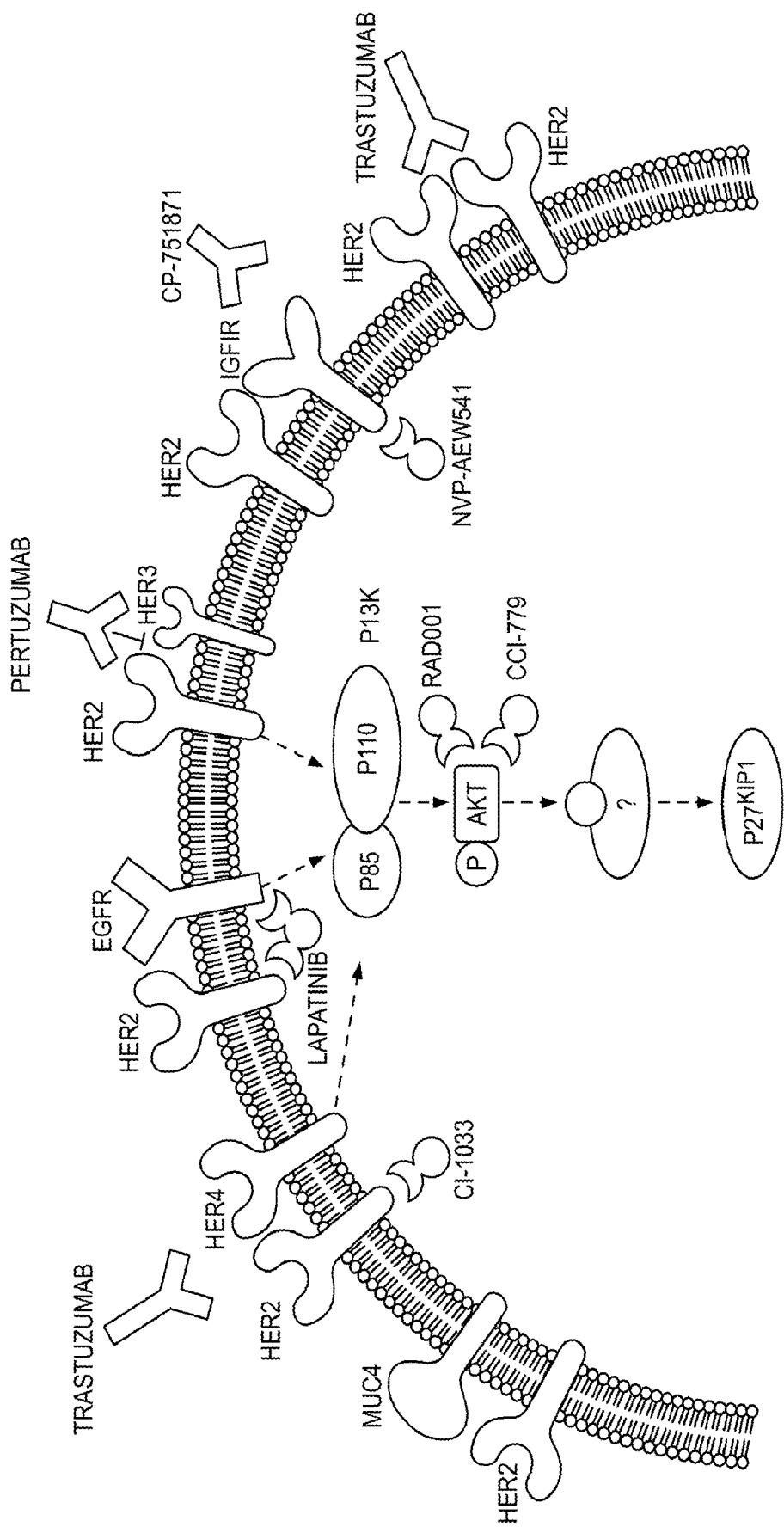
FIG. 2 is a schematic of HER signaling and drugs targeting the receptors (Nahta, *Nature Clin. Pract. Oncol.*, 3(5):269-80 (2006)).

Examples of CD340 polypeptide inhibitors (e.g., HER2 polypeptide inhibitors) include, without limitation, trastuzumab (Herceptin), pertuzumab (Perjeta), Lapatinib (Tykerb or Tyverb), Afatnib (Gilotrif), Saptinib, Erlotinib, Gerfitinib, and Neratinib. In some cases, two or more CD340 polypeptide inhibitors (e.g., two, three, four, five, or more CD340 polypeptide inhibitors) can be administered to a mammal in combination with or sequentially with an USP7 polypeptide inhibitor to reduce the number of cancer cells present within the mammal. A schematic showing HER polypeptides and their ligands is set forth in FIG. 1, and a schematic of HER polypeptide signaling is set forth in FIG. 2.

In some cases, one or more USP7 polypeptide inhibitors and one or more CD340 polypeptide inhibitors can be formulated together into a pharmaceutically acceptable composition for administration to a mammal having cancer (e.g., a HER2$^+$ cancer or a Herceptin resistant breast cancer). For example, a therapeutically effective amount of an USP7 polypeptide inhibitor (e.g., P005091) can be formulated together with one or more CD340 polypeptide inhibitors (e.g., Herceptin). A pharmaceutical composition containing both an USP7 polypeptide inhibitor and a CD340 polypeptide inhibitor can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more USP7 polypeptide inhibitors and/or one or more CD340 polypeptide inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more USP7 polypeptide inhibitors and/or one or more CD340 polypeptide inhibitors can be administered locally or systemically. For example, a composition provided herein can be administered locally by injection into tumors. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more USP7 polypeptide inhibitors can be any amount that increases the sensitivity of cancer cells to treatment with an inhibitor of a CD340 polypeptide without producing significant toxicity to the mammal. For example, an effective amount of an USP7 polypeptide inhibitor such as P005091 can be from about 0.25 mg/kg to about 20 mg/kg (e.g. from about 0.5 mg/kg to about 20 mg/kg, from about 0.75 mg/kg to about 20 mg/kg, from about 0.5 mg/kg to about 15 mg/kg, from about 0.5 mg/kg to about 10 mg/kg, from about 0.5 mg/kg to about 5 mg/kg, from about 0.5 mg/kg to about 1 mg/kg, from about 0.6 mg/kg to about 2.0 mg/kg, or from about 0.6 mg/kg to about 1.0 mg/kg). In some cases, from about 0.01 g to about 5.0 g (e.g., from about 0.03 g to about 1.7 g, from about 0.05 g to about 1.7 g, from about 0.1 g to about 1.7 g, from about 0.03 g to about 1.0 g, or from about 0.5 g to about 1.0 g) of an USP7 polypeptide inhibitor can be administered to an average sized human (e.g., about 75-85 kg human) within a 24 hour period of time.

An effective amount of a composition containing one or more CD340 polypeptide inhibitors can be any amount that reduces the number of cancer cells present within the mammal without producing significant toxicity to the mammal. In some cases, an effective amount of a composition containing one or more CD340 polypeptide inhibitors can be an amount that, when used in connection with an USP7 polypeptide inhibitor such as P005091, reduces the number of cancer cells present within the mammal to a level greater than that observed when that amount is used in the absence of the USP7 polypeptide inhibitor.

In some cases, an effective amount of a CD340 polypeptide inhibitor such as Herceptin when used with an USP7 polypeptide inhibitor (either in combination or sequentially) can be from about 0.5 mg/kg to about 10 mg/kg (from about 1 mg/kg to about 10 mg/kg, from about 2 mg/kg to about 10 mg/kg, from about 0.5 mg/kg to about 8 mg/kg, from about 0.5 mg/kg to about 5 mg/kg, from about 2 mg/kg to about 8 mg/kg, from about 3 mg/kg to about 7 mg/kg, or from about 4 mg/kg to about 6 mg/kg). In some cases, from about 0.01 g to about 5 g (e.g., from about 0.1 g to about 5 g, from about 0.5 g to about 5 g, from about 1 g to about 5 g, from about 0.01 g to about 2.5 g, from about 0.01 g to about 1.5 g, or from about 0.1 g to about 1.5 g) of a CD340 polypeptide inhibitor can be administered to an average sized human (e.g., about 75-85 kg human) within a 24 hour period of time. In some case, Herceptin can be used weekly for about 20 to 60 weeks (e.g., about 52 weeks). In some cases, Erlotinib can be used at a dose of about 100 mg orally once daily. In some cases, Lapatinib can be used at a dose from about 1.25 g to about 1.5 g once daily.

If a particular mammal fails to respond to a particular amount, then the amount of USP7 polypeptide inhibitor and/or CD340 polypeptide inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of an USP7 polypeptide inhibitor and/or CD340 polypeptide inhibitor can be any amount that reduces the number of cancer cells present within the mammal without producing significant toxicity to the mammal. For example, the frequency of administration of a combination containing both an USP7 polypeptide inhibitor and a CD340 polypeptide inhibitor can be from about daily to about four times a month.

The frequency of administration of an USP7 polypeptide inhibitor and/or a CD340 polypeptide inhibitor can remain constant or can be variable during the duration of treatment. A course of treatment with a composition containing an USP7 polypeptide inhibitor and/or a CD340 polypeptide inhibitor can include rest periods. For example, a composition containing one or more USP7 polypeptide inhibitors and one or more CD340 polypeptide inhibitors can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more USP7 polypeptide inhibitors can be any duration that increases the sensitivity of cancer cells to treatment with an inhibitor of a CD340 polypeptide without producing significant toxicity to the mammal. In some cases, the effective duration can vary from several days to several weeks. In general, the effective duration for increasing the sensitivity of cancer cells to treatment with an inhibitor of a CD340 polypeptide can range in duration from about one week to about six weeks.

In some cases, an effective duration for administering a composition containing an USP7 polypeptide inhibitors and/or a CD340 polypeptide inhibitor can be any duration that reduces the number of cancer cells present within the mammal without producing significant toxicity to the mammal. In some cases, the effective duration can vary from several days to several weeks. In general, the effective duration for reducing the number of cancer cells present within the mammal can range in duration from about three weeks to about six weeks.

Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment, the number of cancer cells present within a mammal, and/or the severity of one or more symptoms related to the condition being treated (e.g., cancer) can be monitored. Any appropriate method can be used to determine whether or not the number of cancer cells present within a mammal is reduced. For example, imaging techniques can be used to assess the number of cancer cells present within a mammal.

The invention will be further described in the following examples, which do not limit the scope of the invention described in the claims.

EXAMPLES

Example 1

Figure 4A:
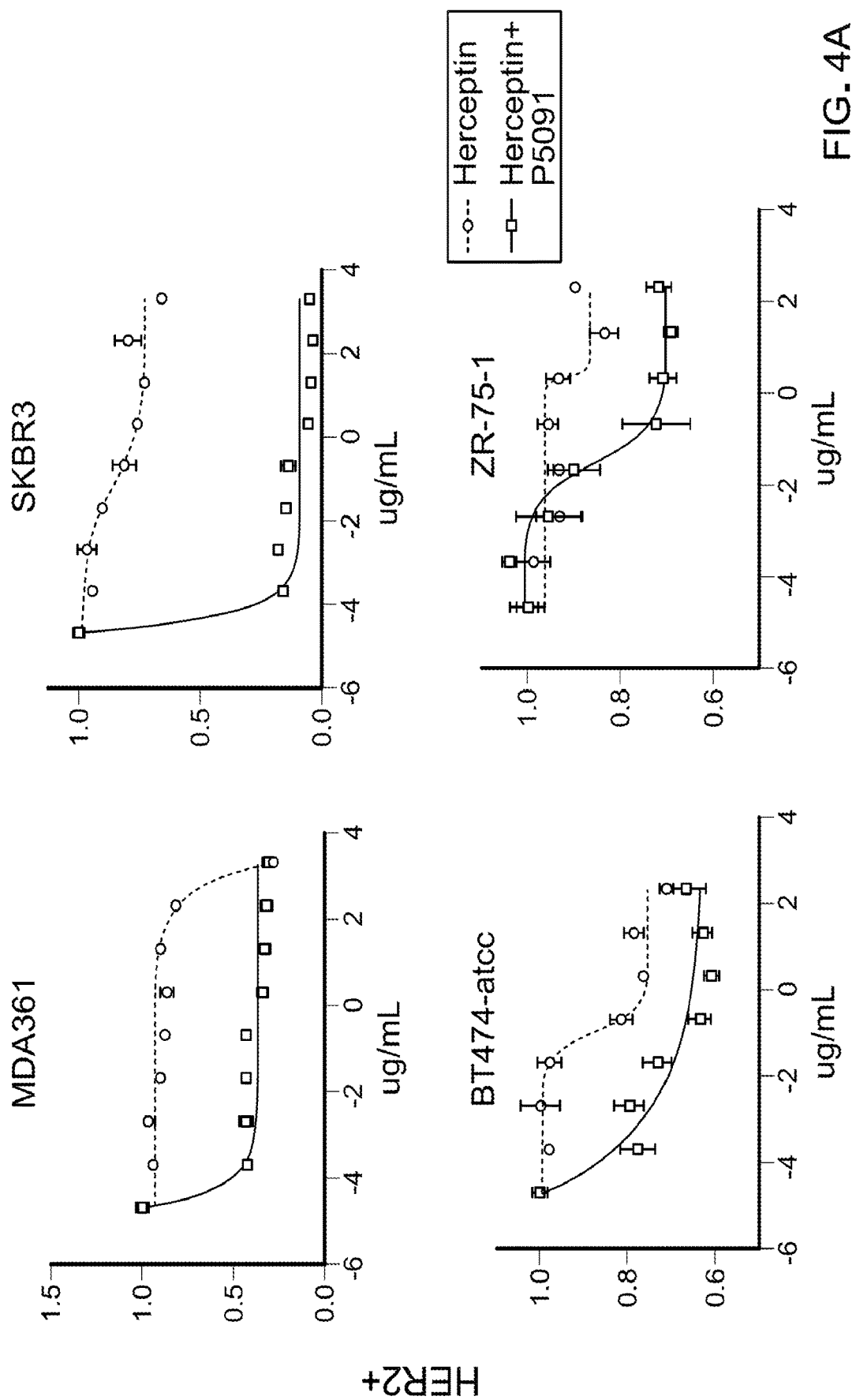

Increasing the Sensitivity of Cancer Cells to Treatment with HER2 Polypeptide Inhibitor P005091 increased the efficacy of the HER2 inhibitor, trastuzumab, in HER2$^+$ breast cancer cells, xenografts, and PDX models. HER2$^+$ breast cancer cells were treated with indicated concentrations of Herceptin with or without 10 µM P005091 for 72 hours. Cell survival was determined by MTS assays. Data was shown as mean values for three independent experiments, and error bars represent standard error of the mean (SEM) (n=3) (FIG. 4A). Tumor xenografts were initiated by subcutaneous inoculation of Bt474 parental and Bt474 Herceptin resistance cells in the lower back of SCID mice. Herceptin (15 mg/kg) and P005091 (10 mg/kg) were administered intraperitoneally once a week for the entire duration of the study. The left panel shows the tumor growth curve for mice implanted with Bt474 parental cells, while the right panel shows the tumor growth curve for mice implanted with Br474 Herceptin resistance cell line (FIG. 4B). A HER2$^+$ patient derived xenograft model was tested by inoculation of tissues in the lower back of SCID mice (FIG. 4C). Drug treatment was same as described above. Data represent the mean±SD of 6 mice in each group.

Figure 5:
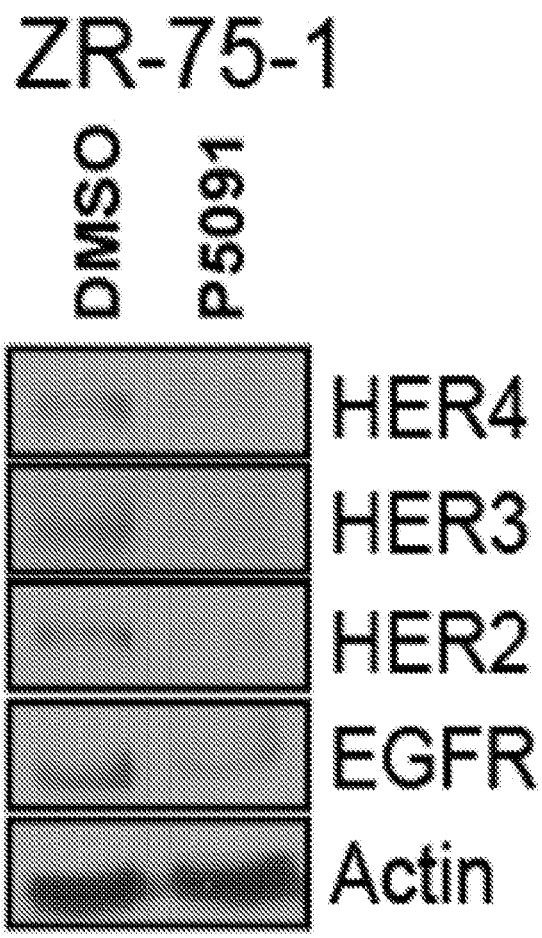
FIG. 5 is a photograph of a Western blot analysis showing that P005091 down regulated HER1 (EGFR), HER2, HER3, and HER4.

Breast cancer cells ZR-75-1 were treated with either 1% DMSO or 10 µM P005091 for 12 hours. Cell lysates were subjected to western blot with indicated antibodies (FIG. 5).

Again, P005091, an USP7 polypeptide inhibitor, dramatically sensitized cells and PDX models to treatment with an HER2 polypeptide inhibitor (i.e., trastuzumab; FIG. 4A-C). This sensitization effect occurred not only in primary HER2$^+$ breast cancer cells, but also in HER2 resistant breast cancer cell lines (FIG. 4A). At the mechanistic level, treatment with the P005091 compound destabilized all four HER family members (FIG. 5).

These results demonstrate that the combination therapy of USP7 polypeptide inhibitors and HER2 polypeptide inhibitors can be used to treat HER2$^+$ breast cancer, including HER2$^+$ breast cancers that are resistant to treatment with an HER2 polypeptide inhibitor alone. These results also demonstrate that the combination therapy of USP7 polypeptide inhibitors and HER2 polypeptide inhibitors can be used to treat other cancers expressing HER1, HER2, HER3, and/or HER4 (or with upregulated HER1, HER2, HER3, and/or HER4 expression) such as gastrointestinal cancers (e.g., HER2$^+$ gastrointestinal cancers), lung cancers (e.g., HER2$^+$ lung cancers), and ovarian cancers (e.g., HER2$^+$ ovarian cancers).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, wherein said method comprises:
   (a) administering an USP7 polypeptide inhibitor to said mammal, and
   (b) administering a CD340 polypeptide inhibitor to said mammal,
   wherein said cancer is a breast cancer, gastrointestinal cancer, stomach cancer, salivary duct carcinoma, lung cancer, or ovarian cancer,
   wherein said USP7 polypeptide inhibitor is selected from the group consisting of (1) P005091, (2) HBX 41,108, (3) p22077, (4) N-(4'-(4-hydroxy-4-((1-methyl-4-oxo-1,4-dihydro-5H-pyrazolo[3,4-d]pyrimidin-5-yl)methyl)piperidine-1-carbonyl)-[1,1'-biphenyl]-2-yl)ethenesulfonamide or a tautomer thereof or a pharmaceutically acceptable salt thereof or a pharmaceutically acceptable salt of the tautomer thereof, (5) (R)-5-((1-(4,4-difluoro-3-(3-fluoro-1H-pyrazol-1-yl)butanoyl)-4-hydroxypiperidin-4-yl)methyl)-1-p-tolyl-1H-pyrazolo[3,4-d]pyrimidin-4(5H)-one or a tautomer thereof or a pharmaceutically acceptable salt thereof or a pharmaceutically acceptable salt of the tautomer thereof, (6) (S)-5-((1-(4,4-difluoro-3-(3-fluoro-1H-pyrazol-1-yl)butanoyl)-4-hydroxypiperidin-4-yl)methyl)-1-p-tolyl-1H-pyrazolo[3,4-d]pyrimidin-4(5H)-one or a tautomer thereof or a pharmaceutically acceptable salt thereof or a pharmaceutically acceptable salt of the tautomer thereof, (7) 1-(4-fluorophenyl)-5-({4-hydroxy-1-[(1r,4r)-4-[(6-fluoropyridin-2-yl)amino]cyclohexanecarbonyl]piperidin-4-yl}methyl)-1H,4H,5H-pyrazolo[3,4-d]pyrimidin-4-one or a tautomer thereof or a pharmaceutically acceptable salt thereof or a pharmaceutically acceptable salt of the tautomer thereof, (8) 1-(4-fluorophenyl)-5-({4-hydroxy-1-[(1s,4s)-4-[(6-fluoropyridin-2-yl)amino]cyclohexanecarbonyl]piperidin-4-yl}methyl)-1H,4H,5H-pyrazolo[3,4-d]pyrimidin-4-one or a tautomer thereof or a pharmaceutically acceptable salt thereof or a pharmaceutically acceptable salt of the tautomer thereof, (9) 1-{3-[(4,4-difluorocyclohexyl)oxy]phenyl}-5-{[4-hydroxy-1-(1-methylcyclopropanecarbonyl)piperidin-4-yl]methyl}-1H,4H,5H-pyrazolo[3,4-d]pyrimidin-4-one or a tautomer thereof or a pharmaceutically acceptable salt thereof or a pharmaceutically acceptable salt of the tautomer thereof, (10) 5-({1-[(3R)-4,4-difluoro-3-(3-fluoro-1H-pyrazol-1-yl)butanoyl]-4-hydroxypiperidin-4-yl}methyl)-1-[4-(trifluoromethyl)phenyl]-1H,4H,5H-pyrazolo[3,4-d]pyrimidin-4-one or a tautomer thereof or a pharmaceutically acceptable salt thereof or a pharmaceutically acceptable salt of the tautomer thereof, (11) 1-(4-fluorophenyl)-5-({4-hydroxy-1-[(1r,4r)-4-{[6-(azetidin-1-yl)pyridin-2-yl]oxy}cyclohexanecarbonyl]piperidin-4-yl}methyl)-1H,4H,5H-pyrazolo[3,4-d]pyrimidin-4-one or a tautomer thereof or a pharmaceutically acceptable salt thereof or a pharmaceutically acceptable salt of the tautomer thereof, (12) 7-(4-fluorophenyl)-3-({4-hydroxy-1-[(1s,4s)-4-(pyridin-2-yloxy)cyclohexane-carbonyl]piperidin-4-yl}methyl)-3H,4H,7H-pyrrolo[2,3-d]pyrimidin-4-one or a tautomer thereof or a pharmaceutically acceptable salt thereof or a pharmaceutically acceptable salt of the tautomer thereof, (13) anti-5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-]pyrimidin-4-one (isomer B) or a tautomer thereof or a pharmaceutically acceptable salt thereof or a pharmaceutically acceptable salt of the tautomer thereof, (14) 1-(4-fluorophenyl)-5-({4-hydroxy-1-[(1r,4r-4-(pyrazin-2-yloxy)cyclohexanecarbonyl]piperidin-4-yl}methyl)-1H,4H,5H-pyrazolo[3,4-d]pyrimidin-4-one or a tautomer thereof or a pharmaceutically acceptable salt thereof or a pharmaceutically acceptable salt of the tautomer thereof, (15) 7-(4-fluorophenyl)-3-({4-hydroxy-1-[(1r,4r-4-(pyridin-2-yloxy)cyclohexanecarbonyl]piperidin-4-yl}methyl)-3H,4H,7H-pyrrolo[2,3-d]pyrimidin-4-one or a tautomer thereof or a pharmaceutically acceptable salt thereof or a pharmaceutically acceptable salt of the tautomer thereof, (16) 5-({1-[(3R)-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one or a tautomer thereof or a pharmaceutically acceptable salt thereof or a pharmaceutically acceptable salt of the tautomer thereof, (17) 5-{[1-(4-fluorobenzoyl)-4-hydroxypiperidin-4-yl]methyl}-1-(4-methoxyphenyl)-1H,4H,5H-pyrazolo[3,4-d]pyrimidin-4-one or a tautomer thereof or a pharmaceutically acceptable salt thereof or a pharmaceutically acceptable salt of the tautomer thereof, (18) 1-[3-(4,4-difluoropiperidin-1-yl)phenyl]-5-{[4-hydroxy-1-(1-methylcyclopropanecarbonyl)piperidin-4-yl]methyl}-1H,4H,5H-pyrazolo[3,4-d]pyrimidin-4-one or a tautomer thereof or a pharmaceutically acceptable salt thereof or a pharmaceutically acceptable salt of the tautomer thereof, (19) 5-({1-[(3R)-4,4-difluoro-3-(4-methyl-1H-pyrazol-1-yl)butanoyl]-4-hydroxypiperidin-4-yl}methyl)-1-(4-fluorophenyl)-1H,4H, 5H-pyrazolo[3,4-d]pyrimidin-4-one or a tautomer thereof or a pharmaceutically acceptable salt thereof or a pharmaceutically acceptable salt of the tautomer thereof, (20) 5-({4-hydroxy-1-[(1r,4r-4-[(6-fluoropyridin-2-yl)oxy]cyclohexanecarbonyl]piperidin-4-yl}methyl)-1-phenyl-1H,4H,5H-pyrazolo[3,4-d]pyrimidin-4-one or a tautomer thereof or a pharmaceutically acceptable salt thereof or a pharmaceutically acceptable salt of the tautomer thereof, (21) 3-({1-[(3S)-4,4-difluoro-3-(3-fluoro-1H-pyrazol-1-yl)butanoyl]-4-hydroxypiperidin-4-yl}methyl)-7-(4-fluorophenyl)-3H,4H,7H-pyrrolo[2,3-d]pyrimidin-4-one or a tautomer thereof or a pharmaceutically acceptable salt thereof or a pharmaceutically acceptable salt of the tautomer thereof, (22) 5-{[4-hydroxy-1-(1-methylcyclopropanecarbonyl)piperidin-4-yl]methyl}-1-[4-(4-methylpiperazin-1-yl)phenyl]-1H,4H,5H-pyrazolo[3,4-d]pyrimidin-4-one or a tautomer thereof or a pharmaceutically acceptable salt thereof or a pharmaceutically acceptable salt of the tautomer thereof, (23) 3-((4-hydroxy-1-(3-(1-methyl-1H-indol-2-yl)benzoyl)piperidin-4-yl)methyl)pyrrolo[2,1-f][1,2,4]triazin-4(3H)-one or a tautomer thereof or a pharmaceutically acceptable salt thereof or a pharmaceutically acceptable salt of the tautomer thereof, (24) (R)-3-((4-hydroxy-1-(3-phenylbutanoyl)piperidin-4-yl)methyl)pyrrolo[2,1-f][1,2,4]triazin-4(3H)-one, (24) 3-((1-(3-(1H-pyrrol-1-yl)butanoyl)-4-hydroxypiperidin-4-yl)methyl)pyrrolo[2,1-f][1,2,4]triazin-4(3H)-one or a tautomer thereof or a pharmaceutically acceptable salt thereof or a pharmaceutically acceptable salt of the tautomer thereof, (25) 3-((4-hydroxy-1-(3-phenylbutanoyl)piperidin-4-yl)methyl)-7-methylpyrrolo[2,1-f][1,2,4]triazin-4(3H)-one, (26) (R)—N-(3-((4-hydroxy-1-(3-phenylbutanoyl)piperidin-4-yl)methyl)-4-oxo-3,4-dihydropyrrolo[2,1-f][1,2,4]triazin-6-yl)acetamide or a tautomer thereof or a pharmaceutically acceptable salt thereof or a pharmaceutically acceptable salt of the tautomer thereof, and (27) (R)-1-(3-((4-hydroxy-1-(3-phenylbutanoyl)piperidin-4-yl)methyl)-4-oxo-3,4-dihydropyrrolo[2,1-f][1,2,4]triazin-6-yl)-3-methylurea or a tautomer thereof or a pharmaceutically acceptable salt thereof or a pharmaceutically acceptable salt of the tautomer thereof, wherein said CD340 polypeptide inhibitor is selected from the group consisting of trastuzumab, pertuzumab, Lapatinib, Afatinib, Sapitinib, Erlotinib, Gefitinib, and Neratinib, and wherein the number of cancer cells within said mammal is reduced to a greater level than the level observed in a comparable mammal administered said CD340 polypeptide inhibitor in the absence of administration of said USP7 polypeptide inhibitor.

2. The method of claim 1, wherein said mammal is a human.

3. The method of claim 1, wherein said cancer is breast cancer.

4. The method of claim 1, wherein said cancer is a HER2$^+$ cancer.

5. The method of claim 1, wherein said cancer is resistant to trastuzumab when administered as the sole active ingredient.

6. The method of claim 1, wherein said USP7 polypeptide inhibitor is P005091.

7. The method of claim 1, wherein said CD340 polypeptide inhibitor is trastuzumab.

* * * * *